US012751910B2

(12) United States Patent
Jung et al.

(10) Patent No.: US 12,751,910 B2
(45) Date of Patent: Oct. 6, 2026

(54) ADDITIVE COMPOSITION FOR IMPROVING BUBBLE DENSITY AND BUBBLE ELASTICITY AND COMPOSITION FOR SKIN CLEANSING

(71) Applicant: AMOREPACIFIC CORPORATION, Seoul (KR)

(72) Inventors: Bokyung Jung, Yongin-si (KR); Daekyeong Kim, Yongin-si (KR); Hyoyoung Park, Yongin-si (KR); Hyunju Yu, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 333 days.

(21) Appl. No.: 18/533,357

(22) Filed: Dec. 8, 2023

(65) Prior Publication Data

US 2024/0189209 A1 Jun. 13, 2024

(30) Foreign Application Priority Data

Dec. 9, 2022 (KR) ........................ 10-2022-0171830

(51) Int. Cl.

| | |
|---|---|
| ***A61Q 5/00*** | (2006.01) |
| ***A61K 8/44*** | (2006.01) |
| ***A61K 8/73*** | (2006.01) |
| ***A61Q 5/02*** | (2006.01) |
| ***A61Q 19/10*** | (2006.01) |

(52) U.S. Cl.

CPC ................ *A61K 8/737* (2013.01); *A61K 8/44* (2013.01); *A61K 8/447* (2013.01); *A61Q 5/02* (2013.01); *A61Q 19/10* (2013.01)

(58) Field of Classification Search

CPC .......... A61K 8/737; A61K 8/44; A61K 8/447; A61K 8/466; A61K 8/73; A61K 2800/594; A61K 8/46; A61K 2800/59; A61Q 5/02; A61Q 19/10

USPC .......................................... 510/119, 120, 121

See application file for complete search history.

(56) References Cited

U.S. PATENT DOCUMENTS 7,964,545 B2 6/2011 Uchiyama et al.
2017/0304173 A1* 10/2017 Elder ....................... A61K 8/86

(Continued)

FOREIGN PATENT DOCUMENTS

| | | |
|---|---|---|
| JP | 6781976 B2 | 11/2020 |
| KR | 10-1421751 B1 | 7/2014 |
| KR | 10-2018-0100665 A | 9/2018 |

(Continued)

OTHER PUBLICATIONS

Office Action issued for Korean Patent Application No. 10-2022-0171830 (Dec. 3, 2024).

*Primary Examiner* — Eisa B Elhilo

(74) *Attorney, Agent, or Firm* — Merchant & Gould P.C.

(57) ABSTRACT

The present disclosure relates to an additive composition for improving bubble density and bubble elasticity that can enhance overall bubble satisfaction through a combination of natural gums, and a composition for skin cleansing. The composition disclosed herein can simultaneously improve the bubble density and the bubble elasticity of the skin cleanser, thereby enhancing the overall bubble satisfaction with the skin cleanser, and comprises the diutan gum, thereby enabling to improve an amount of the bubbles, the bubble density and the bubble elasticity while maintaining weak acidity.

14 Claims, 17 Drawing Sheets

(56) References Cited

U.S. PATENT DOCUMENTS

| | | | | |
|---|---|---|---|---|
| 2020/0170894 | A1* | 6/2020 | Park | A61K 8/466 |
| 2021/0095228 | A1* | 4/2021 | Emiru | B08B 3/08 |

FOREIGN PATENT DOCUMENTS

| | | | |
|---|---|---|---|
| KR | 10-2018-0132924 | A | 12/2018 |
| KR | 10-2303123 | B1 | 9/2021 |
| WO | 2017/189493 | A1 | 11/2017 |
| WO | 2018/080919 | A1 | 5/2018 |

* cited by examiner $M^+$ = Na, K, 1/2 Ca, 1/2 Mg

Diutan gum

Xanthan gum

ADDITIVE COMPOSITION FOR IMPROVING BUBBLE DENSITY AND BUBBLE ELASTICITY AND COMPOSITION FOR SKIN CLEANSING

CROSS REFERENCE TO RELATED APPLICATION

The present application claims the priority of Korean Patent Application No. 10-2022-0171830, filed on Dec. 9, 2022, the entire contents of which is incorporated herein for all purposes by this reference.

BACKGROUND OF THE INVENTION

Field of the Invention

The present disclosure is directed to an additive composition for improving bubble density and bubble elasticity, and a composition for skin cleansing.

Description of the Related Art

In the case of a weakly acidic face cleanser, an amino acid-based surfactant is commonly used in consideration of harmful ingredients and irritation, but has a disadvantage in that its bubble is generally thin to lack elasticity. This is because a size of the hydrophilic group in the amino acid-based surfactant is larger compared to a soap which has dense and elastic bubble, thereby making a interfacial membrane weak and bubble quality relatively poor.

Herein, the bubble quality can be subdivided into bubble quantity, bubble density, and bubble elasticity. In previous studies, there were only cases of enriching the bubble quantity or increasing the bubble density, but there were no cases of improving the bubble elasticity. For example, even though the face cleanser is satisfactory in terms of the overall feeling of use, there are cases where satisfaction for the bubble is relatively low. This is because when the bubble elasticity is low, the overall bubble power is felt to be weak even if an amount of the bubbles is large.

Therefore, since the bubble elasticity contributes to improving the overall bubble satisfaction, it is important to improve the overall bubble satisfaction by increasing both the bubble density and bubble elasticity.

SUMMARY OF THE INVENTION

An aspect of the present disclosure is to provide an additive composition for improving bubble density and bubble elasticity of a weakly acidic skin cleanser, which can enhance not only an amount of the bubbles, but also the bubble density and the bubble elasticity.

An aspect of the present disclosure is to provide a composition for skin cleansing that can objectively quantify the bubble density and the bubble elasticity and has excellent overall bubble satisfaction.

In an aspect, the present disclosure provides an additive composition for improving the bubble density and the bubble elasticity of a weakly acidic skin cleanser, comprising a diutan gum.

In another aspect, the present disclosure provides a composition for skin cleansing, comprising the diutan gum.

In an aspect, an additive composition for improving the bubble density and the bubble elasticity of the weakly acidic skin cleanser disclosed in the present disclosure can simultaneously improve the bubble density and the bubble elasticity of the skin cleanser, thereby enhancing overall bubble satisfaction with the skin cleanser.

In another aspect, a composition for skin cleansing disclosed in the present disclosure comprises the diutan gum, thereby enabling to improve an amount of the bubbles, the bubble density and the bubble elasticity while maintaining weak acidity.

DETAILED DESCRIPTION OF THE INVENTION

Hereinafter, the present disclosure will be described in more detail through the following Examples. However, the Examples are provided only for illustrative purposes to aid understanding of the present disclosure, and the category and scope of the present disclosure are not limited thereto.

Additive Composition for Improving Bubble Density and Bubble Elasticity of Weakly Acidic Skin Cleanser Exemplary embodiments of the present disclosure provide an additive composition for improving bubble density and bubble elasticity of a weakly acidic skin cleanser, comprising a diutan gum.

Figure 1:
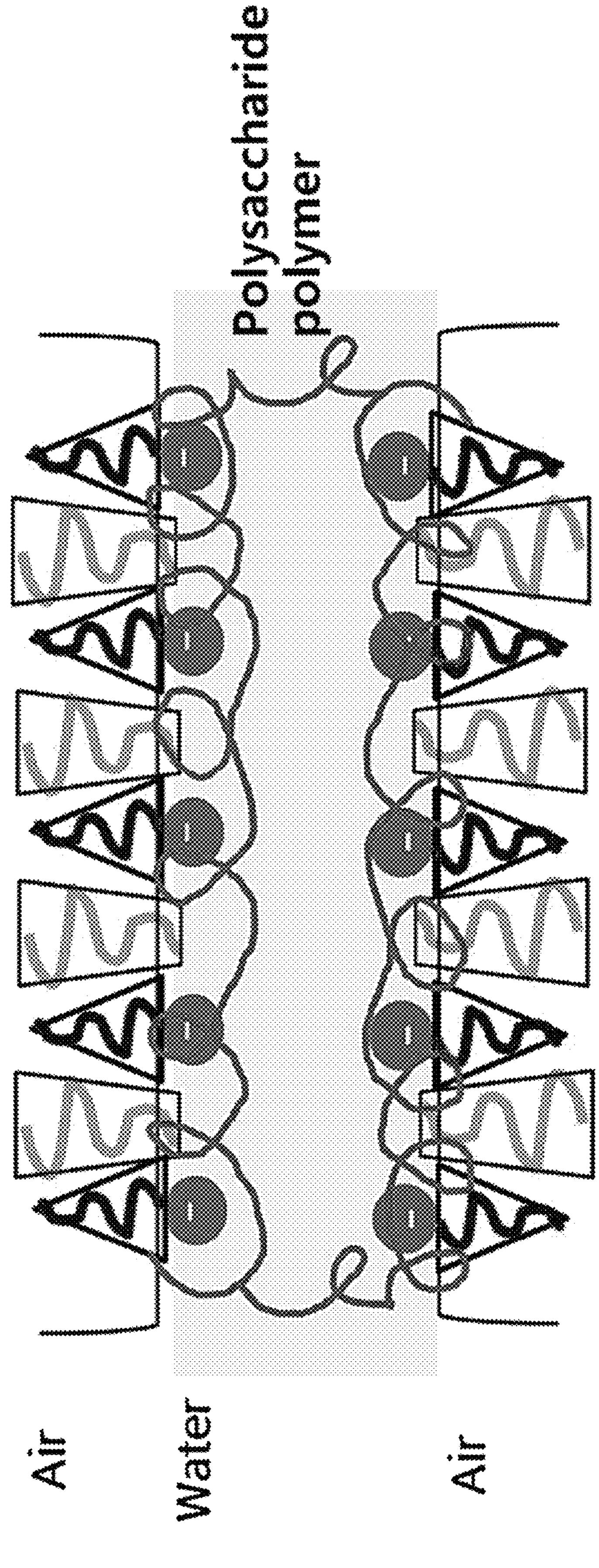
FIG. 1 is a schematic diagram of a polysaccharide polymer according to an embodiment of the present disclosure.

Referring to FIG. 1, a polysaccharide polymer among natural gums has an effect of thickening a water phase and serve to strengthen the water layer between interfacial membranes, because it has much amount of OH groups and a high molecular weight. According to an embodiment of the present disclosure, it is possible to improve not only the bubble density but also the bubble elasticity of the weakly acidic skin cleanser by comprising a diutan gum, a polysaccharide polymer that is particularly effective in improving the bubble elasticity.

In an embodiment, the weakly acidic skin cleanser may be a weakly acidic amino acid-based skin cleanser.

In an embodiment, the composition of the present disclosure may further comprise an amino acid-based surfactant.

In an embodiment, the composition may further comprise a cationic polymer. According to an embodiment of the present disclosure, a repulsion force of the amino acid-based surfactant head, which is an anionic surfactant, can be reduced by using the cationic polymer to strengthen interfacial membranes and help improve a bubble power.

Conventionally, due to a slippery nature of the cationic polymer with a high degree of substitution, there was no choice but to use the cationic polymer with a low degree of substitution. In this case, there was a problem that the bubble elasticity could not be sufficiently maintained. Specifically, if the degree of substitution of the cationic polymer is high or a structure is not well packed in a straight line, the interfacial membranes widen and the bubble can be easily dissipated, whereby the conventional skin cleanser could not use a gua polymer with the high degree of substitution due to its slippery feeling of use. Therefore, a polymer is needed to act as a bridge that can hold the water layer between the interfacial membranes. According to an embodiment of the present disclosure, a diutan gum plays that role to improve both of the bubble density and the bubble elasticity.

In an embodiment, the cationic polymer may be a guar gum. Unlike the other cationic polymers that only have an effect on the bubble density, the guar gum can improve the bubble elasticity more than the other cationic polymers.

In an embodiment, the composition further comprises the cationic polymer, and a weight ratio of the cationic polymer and the diutan gum may be 1:0.5 to 2.

For example, the weight ratio of the cationic polymer and the diutan gum may be 1:0.5 or more, 1:0.6 or more, 1:0.7 or more, 1:0.8 or more, 1:0.9 or more, 1:1 or more, 1:1.1 or more, 1:1.2, or more, 1:1.3 or more, 1:1.4 or more, 1:1.5 or more, 1:1.6 or more, 1:1.7 or more, 1:1.8 or more, or 1:1.9 or more, and may be 1:2 or less, 1:1.9 or less, 1:1.8 or less, 1:1.7 or less, 1:1.6 or less, 1:1.5 or less, 1:1.4 or less, 1:1.3 or less, 1:1.2 or less, 1:1.1 or less, 1:1 or less, 1:0.9 or less, 1:0.8 or less, 1:0.7 or less, or 1:0.6 or less.

If the weight ratio of the cationic polymer and the diutan gum is less than 1:0.5, both the bubble density and/or bubble elasticity may be reduced, especially the bubble elasticity may be reduced, and if it is more than 1:2, both the bubble density and/or bubble elasticity may be reduced.

In an embodiment, the composition further comprises the cationic polymer, and a total weight of the cationic polymer and the diutan gum may be 0.05 to 1% by weight based on the total weight of the composition.

For example, the total weight of the cationic polymer and the diutan gum may be 0.05% by weight or more, 0.1% by weight or more, 0.15% by weight or more, 0.2% by weight or more, 0.25% by weight or more, 0.3% by weight or more, 0.35% by weight or more, or 0.4% by weight or more, and may be 1% by weight or less, 0.5% by weight or less, 0.45% by weight or less, 0.4% by weight or less, 0.35% by weight or less, 0.3% by weight or less, 0.25% by weight or less, 0.2% by weight or less, 0.15% by weight or less, or 0.1% by weight or less.

If the total weight of the cationic polymer and the diutan gum is less than 0.05% by weight, there is no effect on the bubble, and if it is more than 1% by weight, a formulation is not slippery and lumpy, which may provide an unpleasant touch feeling to a consumer.

In an embodiment, a pH of the composition may be 4 to 7.

For example, the pH of the composition may be 4 or higher, 4.5 or higher, 4.7 or higher, 4.9 or higher, 5.1 or higher, 5.3 or higher, 5.5 or higher, 5.7 or higher, 5.9 or higher, 6.1 or higher, or 6.3 or higher, and may be 7 or lower, 6.5 or lower, 6.3 or lower, 6.1 or lower, 5.9 or lower, 5.7 or lower, 5.5 or lower, 5.3 or lower, 5.1 or lower, 4.9 or lower, or 4.7 or lower.

The composition can maintain excellent overall bubble quality by improving not only the bubble density but also the bubble elasticity while maintaining weak acidity at the above pH.

In an embodiment, the bubble elasticity of the composition may be 11,000 cps or more as measured by a BROOKFIELD LV viscometer.

In an embodiment, the viscosity may be measured using the BROOKFIELD LV viscometer at a room temperature while rotating at 3 rpm using spindle number 3.

For example, the bubble elasticity may be 11,000 cps or more, 11,500 cps or more, 12,000 cps or more, 12,500 cps or more, 13,000 cps or more, or 13,500 cps or more.

If the bubble elasticity is less than 11,000 cps, the overall bubble satisfaction may be low even if an amount of the bubbles is large.

In an embodiment, the weakly acidic skin cleanser may be a hair cleanser, a body cleanser, a hand cleanser, or a face cleanser.

The additive composition for improving the bubble density and the bubble elasticity of the weakly acidic skin cleanser according to an embodiment of the present disclosure may further comprise, as a carrier component, aliphatic alcohol sulfate, aliphatic alcohol ether sulfate, sulfosuccinic acid monoester, isethionate, an imidazolinium derivative, methyl taurate, sarcosinate, fatty acid amide ether sulfate, alkylamidobetaine, aliphatic alcohol, fatty acid glyceride, fatty acid diethanolamide, a vegetable oil, a linoline derivative, ethoxylated glycerol fatty acid ester, etc.

The additive composition for improving the bubble density and the bubble elasticity of the weakly acidic skin cleanser according to an embodiment of the present disclosure may further comprise components included in functional additives in addition to the above components. The functional additive may include components selected from the group consisting of a water-soluble vitamin, an oil-soluble vitamin, a polymer peptide, a polymer polysaccharide, a sphingolipid, and a seaweed extract.

The additive composition for improving the bubble density and the bubble elasticity of the weakly acidic skin cleanser according to an embodiment of the present disclosure may also comprise components included in a general cleanser composition, if necessary, in addition to the functional additives. Other components comprised in the additive composition may include an oil and fat component, a moisturizer, an emollient, organic and inorganic pigments, an organic powder, a ultraviolet absorber, a preservative, a disinfectant, an antioxidant, a plant extract, a pH adjuster, an alcohol, a pigment, a fragrance, a blood circulation promoter, a cooling sensitizer, an antiperspirant, a purified water, etc.

Composition for Skin Cleansing

Exemplary embodiments of the present disclosure provide a composition for skin cleansing, comprising a diutan gum.

In an embodiment, the composition for skin cleansing may further comprise an amino acid-based surfactant.

In an embodiment, the composition for skin cleansing may further comprise a cationic polymer.

In an embodiment, the cationic polymer may be a guar gum.

In an embodiment, the composition for skin cleansing further comprises the cationic polymer, and a weight ratio of the cationic polymer and the diutan gum may be 1:0.5 to 2.

For example, the weight ratio of the cationic polymer and diutan gum may be 1:0.5 or more, 1:0.6 or more, 1:0.7 or more, 1:0.8 or more, 1:0.9 or more, 1:1 or more, 1:1.1 or more, 1:1.2, or more, 1:1.3 or more, 1:1.4 or more, 1:1.5 or more, 1:1.6 or more, 1:1.7 or more, 1:1.8 or more, or 1:1.9 or more, and may be 1:2 or less, 1:1.9 or less, 1:1.8 or less, 1:1.7 or less, 1:1.6 or less, 1:1.5 or less, 1:1.4 or less, 1:1.3 or less, 1:1.2 or less, 1:1.1 or less, 1:1 or less, 1:0.9 or less, 1:0.8 or less, 1:0.7 or less, or 1:0.6 or less.

In an embodiment, the composition for skin cleansing further comprises the cationic polymer, and a total weight of the cationic polymer and the diutan gum may be 0.05 to 1% by weight based on the total weight of the composition.

For example, the total weight of the cationic polymer and the diutan gum may be 0.05% by weight or more, 0.1% by weight or more, 0.15% by weight or more, 0.2% by weight or more, 0.25% by weight or more, 0.3% by weight or more, 0.35% by weight or more, or 0.4% by weight or more, and may be 1% by weight or less, 0.5% by weight or less, 0.45% by weight or less, 0.4% by weight or less, 0.35% by weight or less, 0.3% by weight or less, 0.25% by weight or less, 0.2% by weight or less, 0.15% by weight or less, or 0.1% by weight or less.

In an embodiment, a pH of the composition for skin cleansing may be 4 to 7.

For example, the pH of the composition may be 4 or higher, 4.5 or higher, 4.7 or higher, 4.9 or higher, 5.1 or higher, 5.3 or higher, 5.5 or higher, 5.7 or higher, 5.9 or higher, 6.1 or higher, or 6.3 or higher, and may be 7 or lower, 6.5 or lower, 6.3 or lower, 6.1 or lower, 5.9 or lower, 5.7 or lower, 5.5 or lower, 5.3 or lower, 5.1 or lower, 4.9 or lower, or 4.7 or lower.

In an embodiment, the bubble elasticity of the composition for skin cleansing may be 11,000 cps or more when measured by a BROOKFIELD LV viscometer.

For example, the bubble elasticity may be 11.000 cps or more, 11,500 cps or more, 12.000 cps or more, 12,500 cps or more, 13,000 cps or more, or 13.500 cps or more.

In an embodiment, the composition for skin cleansing may be a hair cleanser, a body cleanser, a hand cleanser, or a face cleanser.

An additive composition for improving the bubble density and the bubble elasticity of the composition for skin cleansing according to an embodiment of the present disclosure may further comprise, as a carrier component, aliphatic alcohol sulfate, aliphatic alcohol ether sulfate, sulfosuccinic acid monoester, isethionate, an imidazolinium derivative, methyl taurate, sarcosinate, fatty acid amide ether sulfate, alkylamidobetaine, aliphatic alcohol, fatty acid glyceride, fatty acid diethanolamide, a vegetable oil, a linoline derivative, ethoxylated glycerol fatty acid ester, etc.

The composition for skin cleansing according to an embodiment of the present disclosure may further comprise components included in functional additives in addition to the above components. The functional additive may include components selected from the group consisting of a water-soluble vitamin, an oil-soluble vitamin, a polymer peptide, a polymer polysaccharide, a sphingolipid, and a seaweed extract.

The composition for skin cleansing according to an embodiment of the present disclosure may also comprise components included in a general composition for skin cleansing, if necessary, in addition to the functional additives. Other components comprised in the composition for skin cleansing may include an oil and fat component, a moisturizer, an emollient, organic and inorganic pigments, an organic powder, a ultraviolet absorber, a preservative, a disinfectant, an antioxidant, a plant extract, a pH adjuster, an alcohol, a pigment, a fragrance, a blood circulation promoter, a cooling sensitizer, an antiperspirant, a purified water, etc.

Still other exemplary embodiment of the present disclosure provides a method for improving bubble density and bubble elasticity of a weakly acidic skin cleanser by adding the above-described additive composition to the weakly acidic skin cleanser.

Still another exemplary embodiment of the present disclosure provides a non-therapeutic use of the above-described additive composition for improving bubble density and bubble elasticity of a weakly acidic skin cleanser.

Hereinafter, the present disclosure will be described in more detail through the following Examples. However, the Examples are intended to be provided only for illustrative purposes to aid understanding of the present disclosure, and the category and scope of the present disclosure are not limited thereto.

Example

In the following Examples and Comparative Examples, the properties of bubbles were subdivided to measure an amount of the bubbles, bubble density, and bubble elasticity.

An amount of the bubbles was determined by dropping 2 ml of a composition according to Example or Comparative Example into 50 ml of tap water, mixing the solution without separate dilution, repeating 10 times a process of mixing at 2500 rpm for 10 seconds and stopping for 3 seconds by a DFA (Dynamic Foam Analyzer, KRUSS), and then measuring a height of the bubbles (Unit: mm).

The bubble density was determined by dropping 2 ml of a composition according to Example or Comparative Example into 50 ml of tap water, mixing the solution without separate dilution, repeating 10 times a process of mixing at 2500 rpm for 10 seconds and stopping for 3 seconds by the DFA (Dynamic Foam Analyzer. KRUSS), and then measuring the number of the bubbles per unit area (number/mm).

The bubble elasticity was determined by preparing a solution containing 50 g of a composition according to Example or Comparative Example and 50 g of tap water in a 500 ml of a beaker, mixing the solution at 300 rpm for 1 minute and at 500 rpm for 2 minutes using an Azimixer (HOMO-MIXER & AGITATOR, SWI), and then measuring a viscosity of the bubbles 1 minute later (BROOKFIELD LV viscometer).

1. Adjustment of Arrangement of Surfactant Head

As shown in Table 1 below, a composition containing a fatty acid, a fatty alcohol, an amphoteric surfactant, and a cationic polymer in an anionic surfactant was prepared to indicate degrees of an amount of the bubbles, bubble density, and bubble elasticity according to the following standards.

1. Amount of bubbles→Less than 80: Few. Less than 90: Normal, 90 or more: Much
2. Bubble density→Less than 120: No effect (X), 120 or more: Effective (○), 150 or more: Excellent effect (◎)
3. Bubble elasticity→Less than 8000: No effect (X), 8000-10000: Effective (○). More than 10000: Excellent effect (◎)

TABLE 1

| | Component name | Adjustment of arrangement of surfactant head Comparative Example 1 | Comparative Example 2 | Comparative Example 3 | Comparative Example 4 | Comparative Example 5 |
|---|---|---|---|---|---|---|
| Prescription of weakly acidic amino acid-based cleanser base | Purified water (KP) | to 100 | to 100 | to 100 | to 100 | to 100 |
| | Glycerin | 20.000 | 20.000 | 20.000 | 20.000 | 20.000 |
| | Potassium cocoylglycinate | 15.000 | 15.000 | 15.000 | 15.000 | 15.000 |
| | Laurylhydroxysultaine | 1.000 | 1.000 | 1.000 | 1.000 | 1.000 |
| | Citric acid | 1.500 | 1.500 | 1.500 | 1.500 | 1.500 |
| Fatty acid | Lauric acid | 1.000 | — | — | — | — |
| Fatty alcohol | Cetyl alcohol | — | 1.000 | — | — | — |
| Amphoteric surfactant | Cocamidopropyl betaine | — | — | 1.500 | — | — |
| Polyquaternium cationic polymer | Polyquaternium-7 | — | — | — | 0.200 | — |
| Guar gum | Hydroxypropylguarhydroxypropyltrimonium chloride | — | — | — | — | 0.2 |
| Amount of bubbles | | Normal | Normal | Much | Much | Normal |
| Bubble density | | ○ | ○ | X | ○ | ◎ |
| Bubble elasticity | | X | X | X | X | ○ |
| Slippery | | Good | Good | Slippery | Slippery | Slippery |

As a result of the observation, it was possible to reduce repulsion force of the anionic surfactant head, but it was difficult to improve the bubble elasticity. Specifically, it was confirmed that in the formulation based on the amino acid surfactant, addition of the cationic polymer was most effective in improving the bubble power, and that addition of the polyquaternium polymer was able to increase an amount of the bubbles and the bubble density, but the bubble elasticity was no significant effect.

2. Change in Physical Properties of Water Phase

As shown in Table 2, Table 3, and FIGS. 2A to 2F below, as the polysaccharide polymer a diutan gum (FIG. 2A) (SPHINGOMONAS FERMENT EXTRACT), a xanthan gum (FIG. 2B), and a CMC (CELLULOSE GUM, FIG. 2C) were applied to the composition for skin cleansing. Photographs observing the bubble density of each composition were shown in FIGS. 2D (diutan gum), 2E (xanthan gum), and 2F (CMC), respectively.

TABLE 2

| | Component name | Change in physical properties of water phase Comparative Example 6 | Comparative Example 7 | Example 1 |
|---|---|---|---|---|
| Prescription of weakly acidic amino acid-based cleanser base | Purified water (KP) | to 100 | to 100 | to 100 |
| | Glycerin | 20.000 | 20.000 | 20.000 |
| | Potassium cocoylglycinate | 15.000 | 15.000 | 15.000 |
| | Laurylhydroxysultaine | 1.000 | 1.000 | 1.000 |
| | Citric acid | 1.500 | 1.500 | 1.500 |
| Xanthan gum | Xanthan gum | 0.200 | — | — |
| CMC | Cellulose gum | — | 0.200 | — |
| Diutan gum | Diutan gum | — | — | 0.2 |
| Amount of bubbles | | Normal | Normal | Normal |
| Bubble density | | 135 | 107 | 159 |
| Bubble elasticity | | 10,300 | 8,300 | 12,000 |
| Slippery | | Slippery | Slippery | Good |

As a result of the observation, it was confirmed that an effect of improving the bubble density and the bubble elasticity of the diutan gum was superior to that of the other gums.

TABLE 3

Figure 2A:
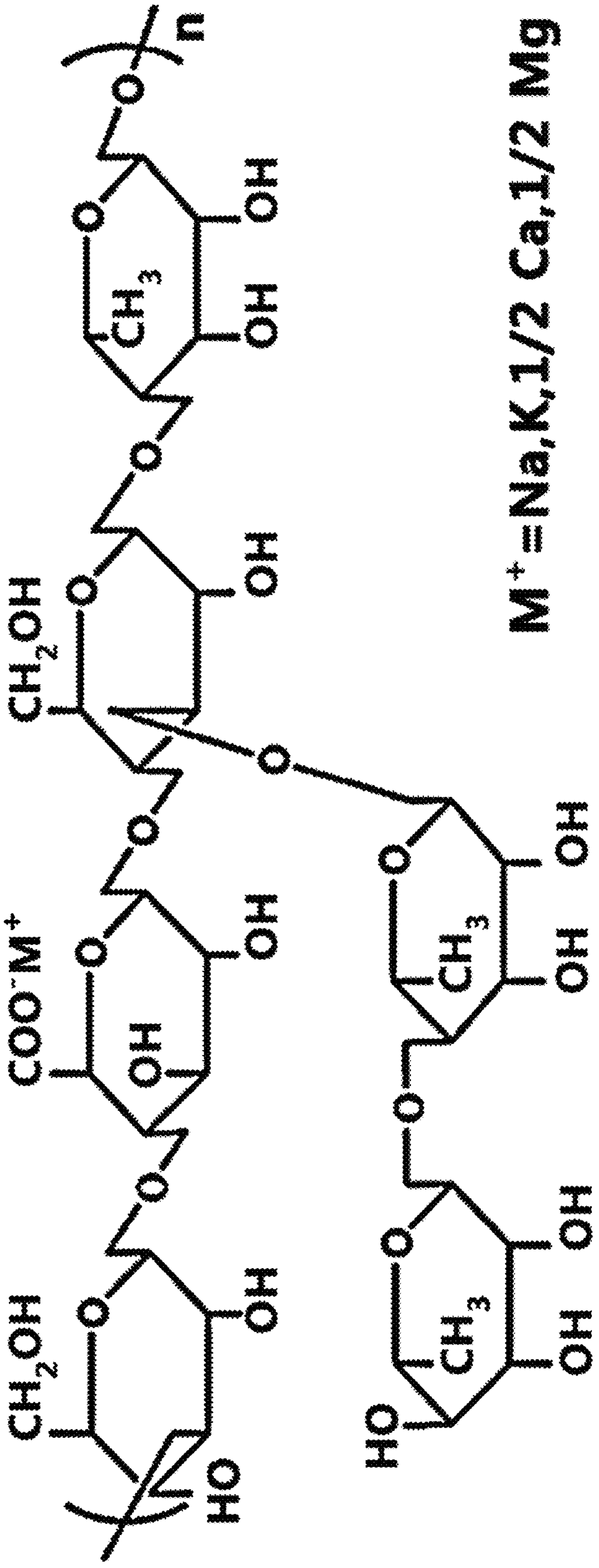
FIGS. 2A to 2C show the structural formulas of a diutan gum (2A), a xanthan gum (2B), and a CMC (2C) that are used in an embodiment of the present disclosure.
Figure 2B:
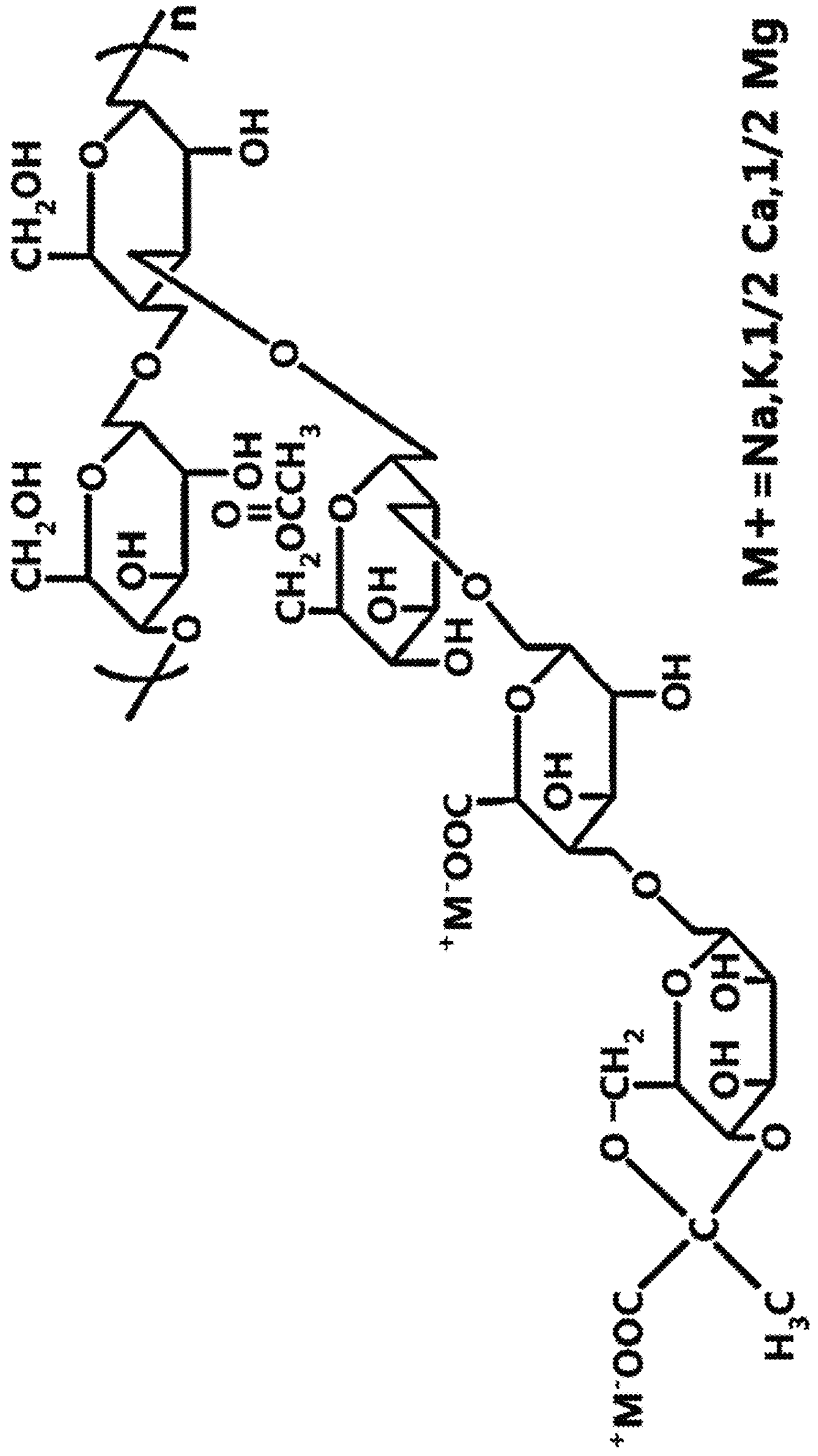
Figure 2C:
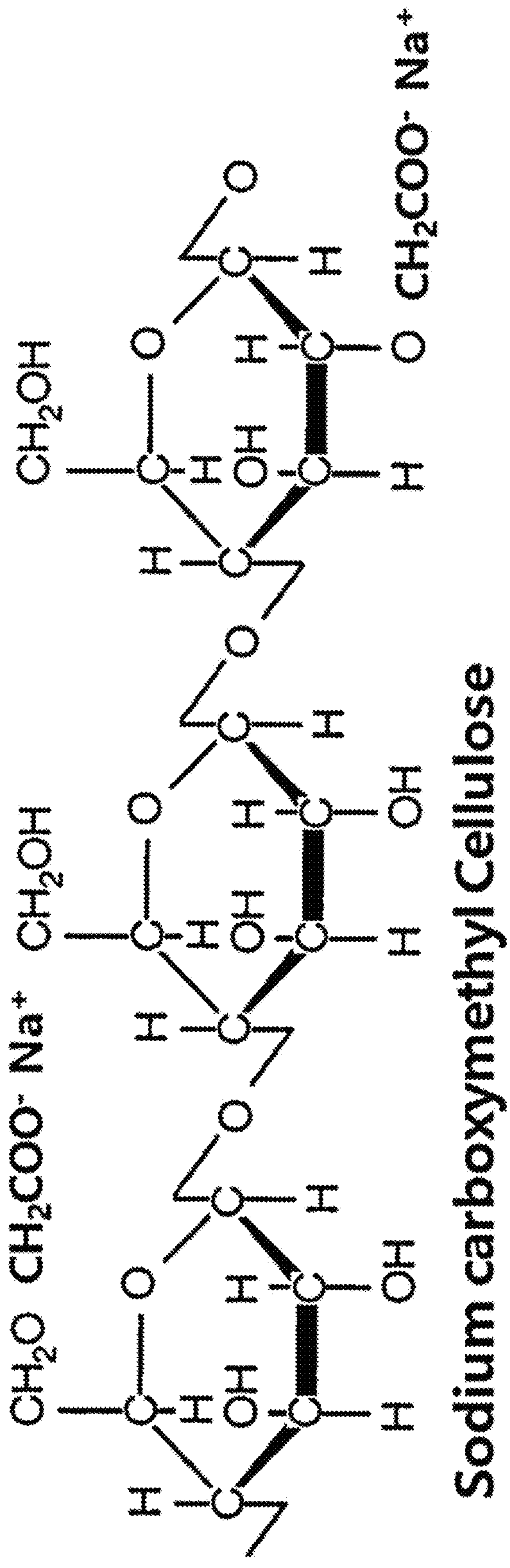
Figure 2D:
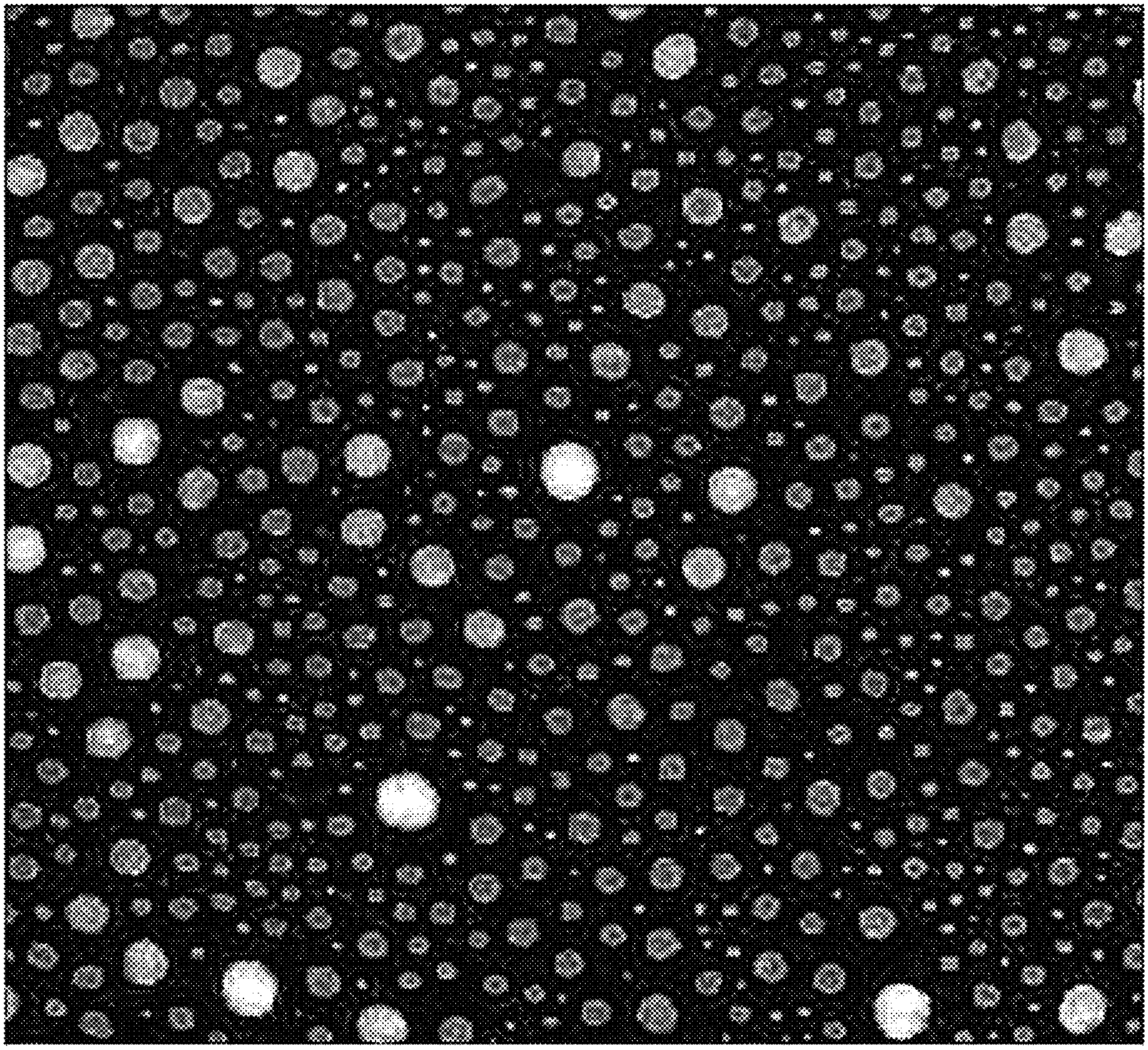
FIGS. 2D to 2F show the result of observing bubble density of a composition according to an embodiment of the present disclosure.
Figure 2E:
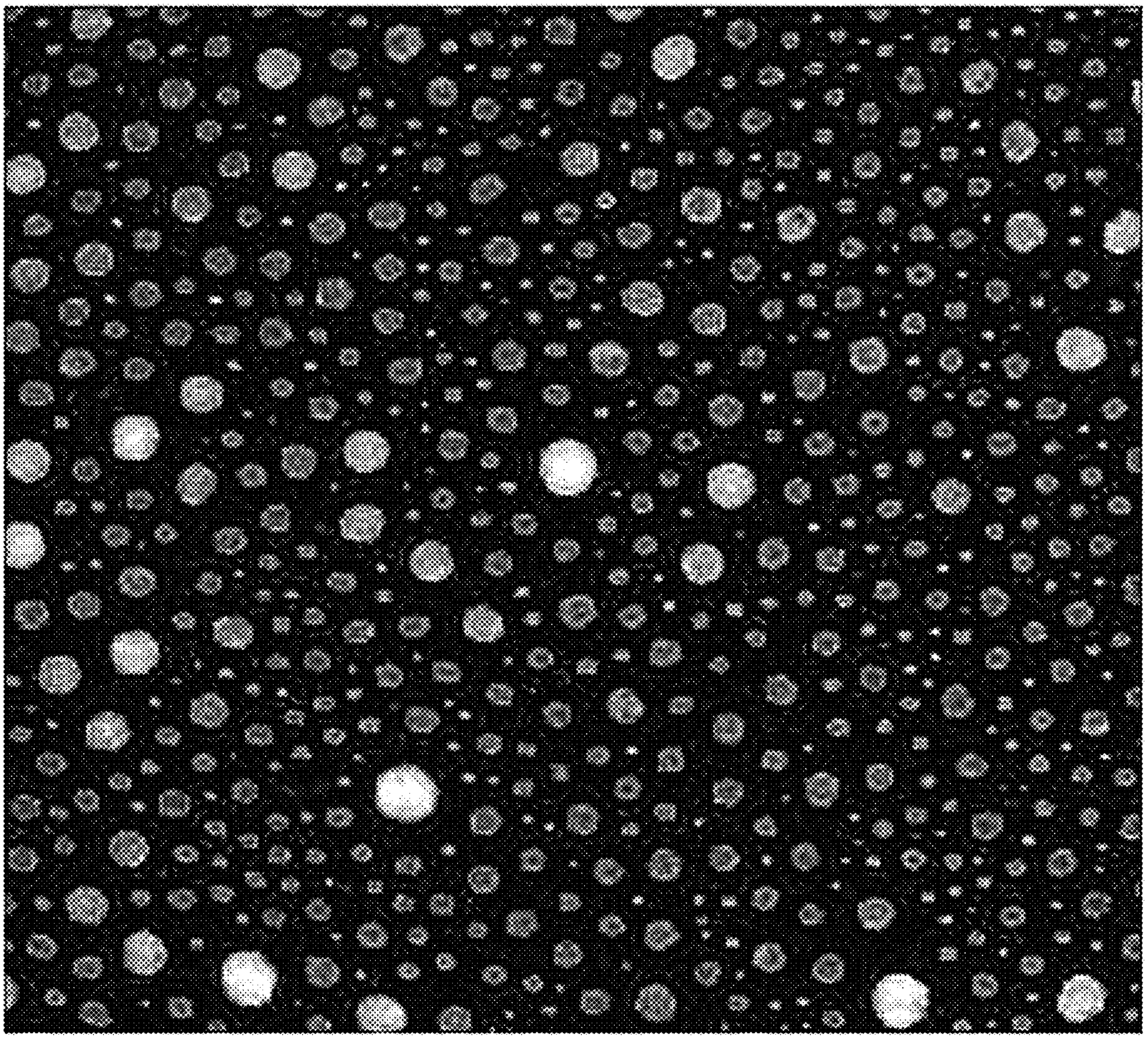
Figure 2F:
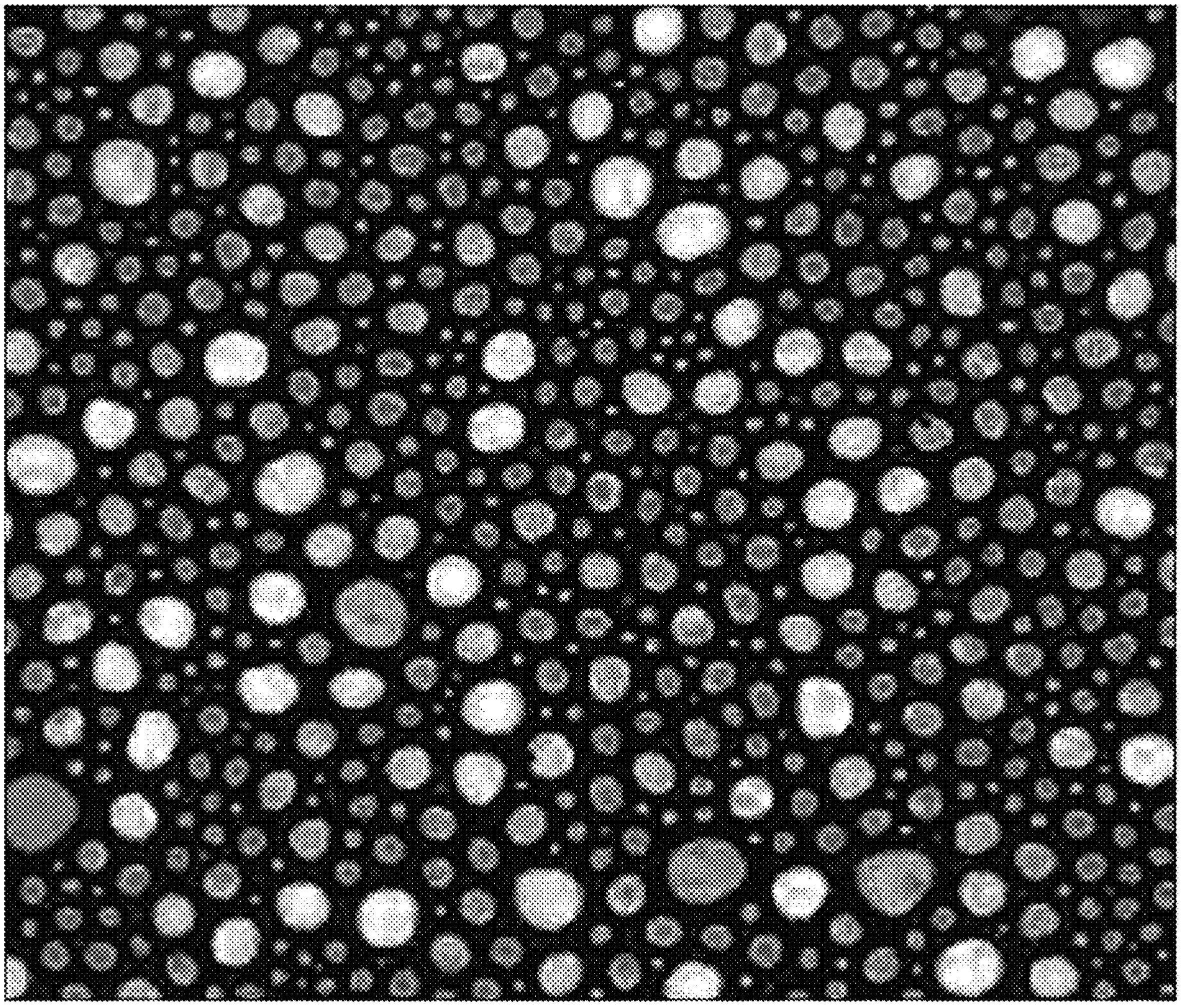
Figure 3A:
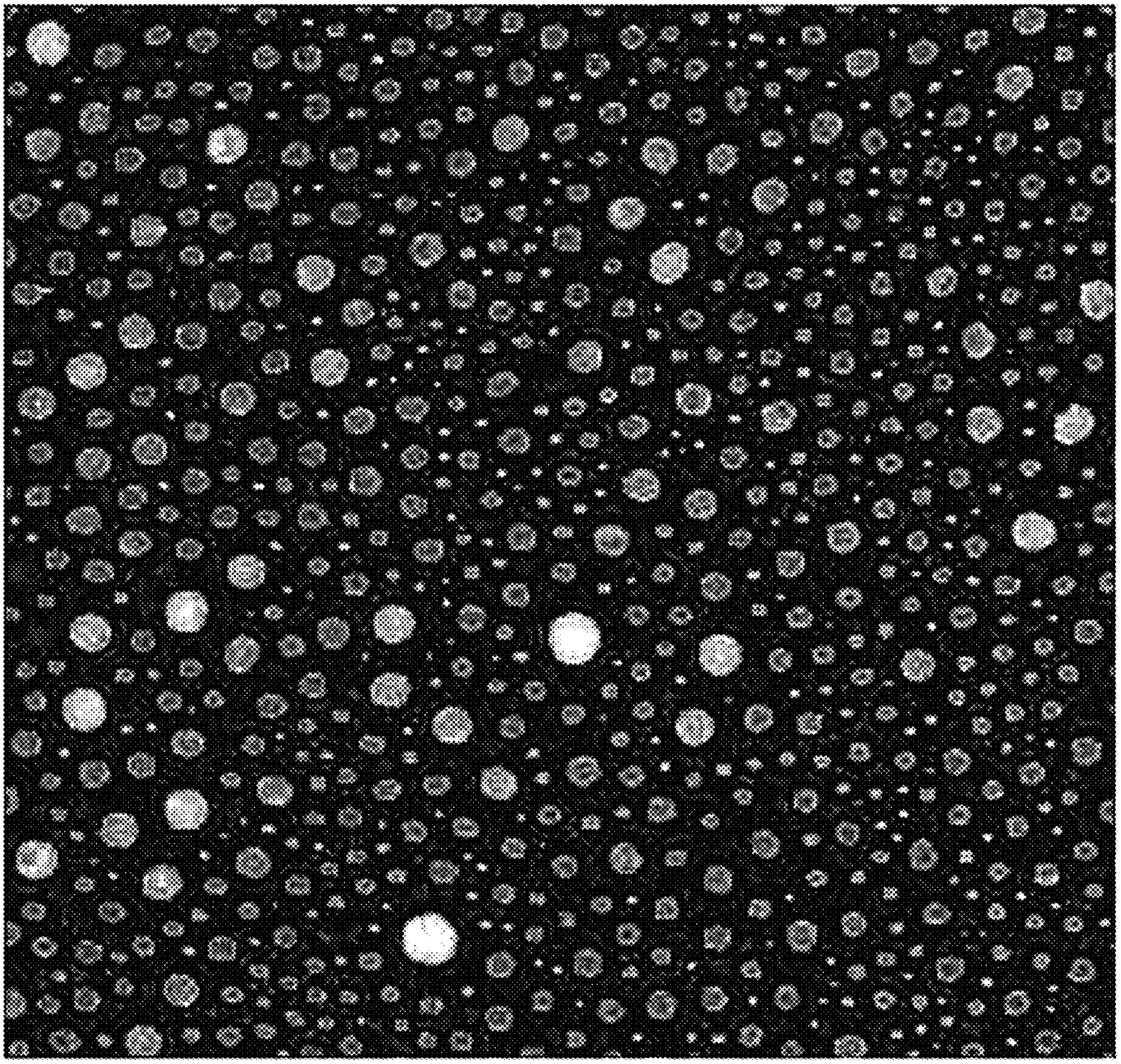
FIGS. 3A to 3F show the result of observing bubble density of a composition according to an embodiment of the present disclosure.
Figure 3B:
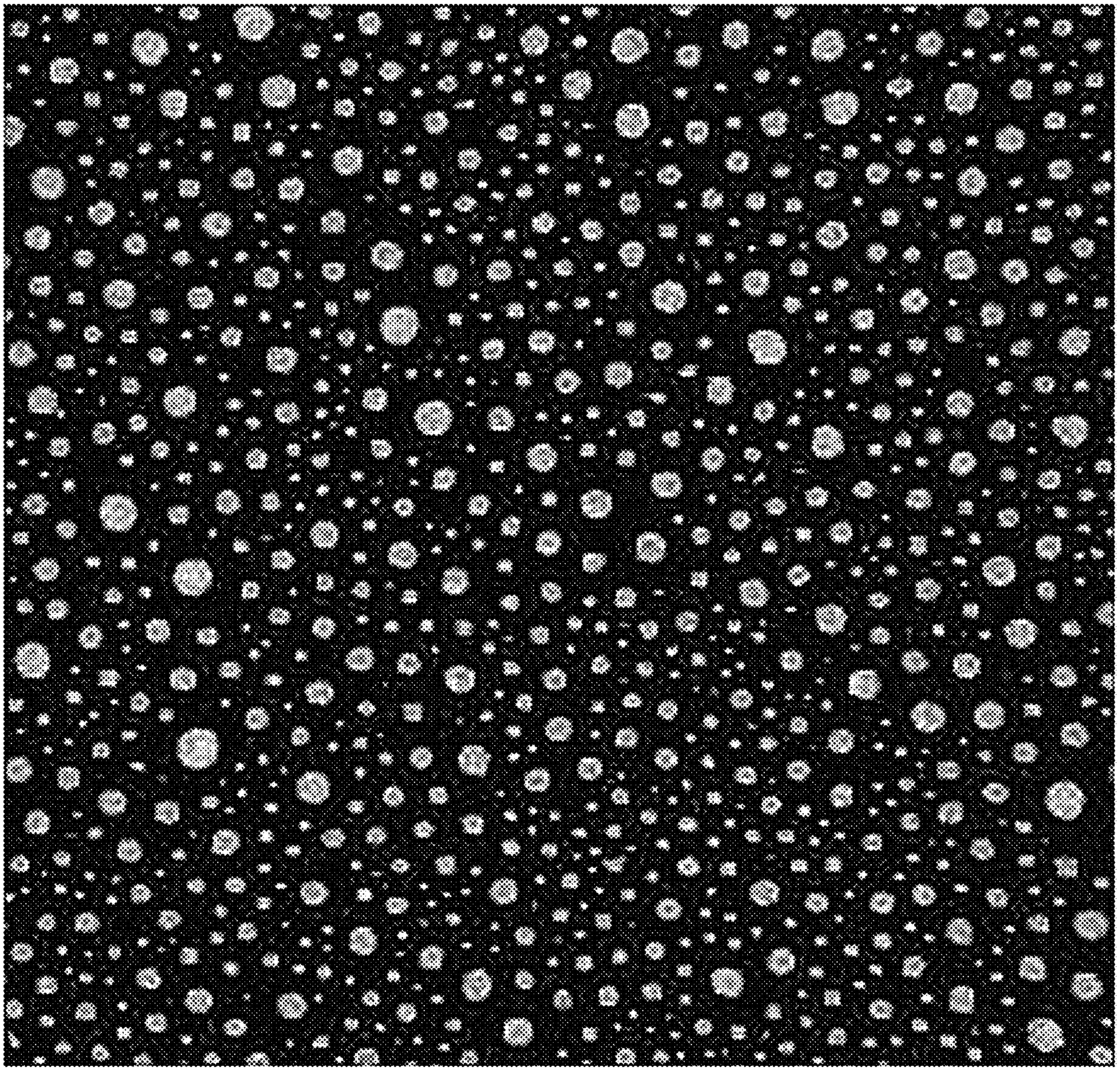
Figure 3C:
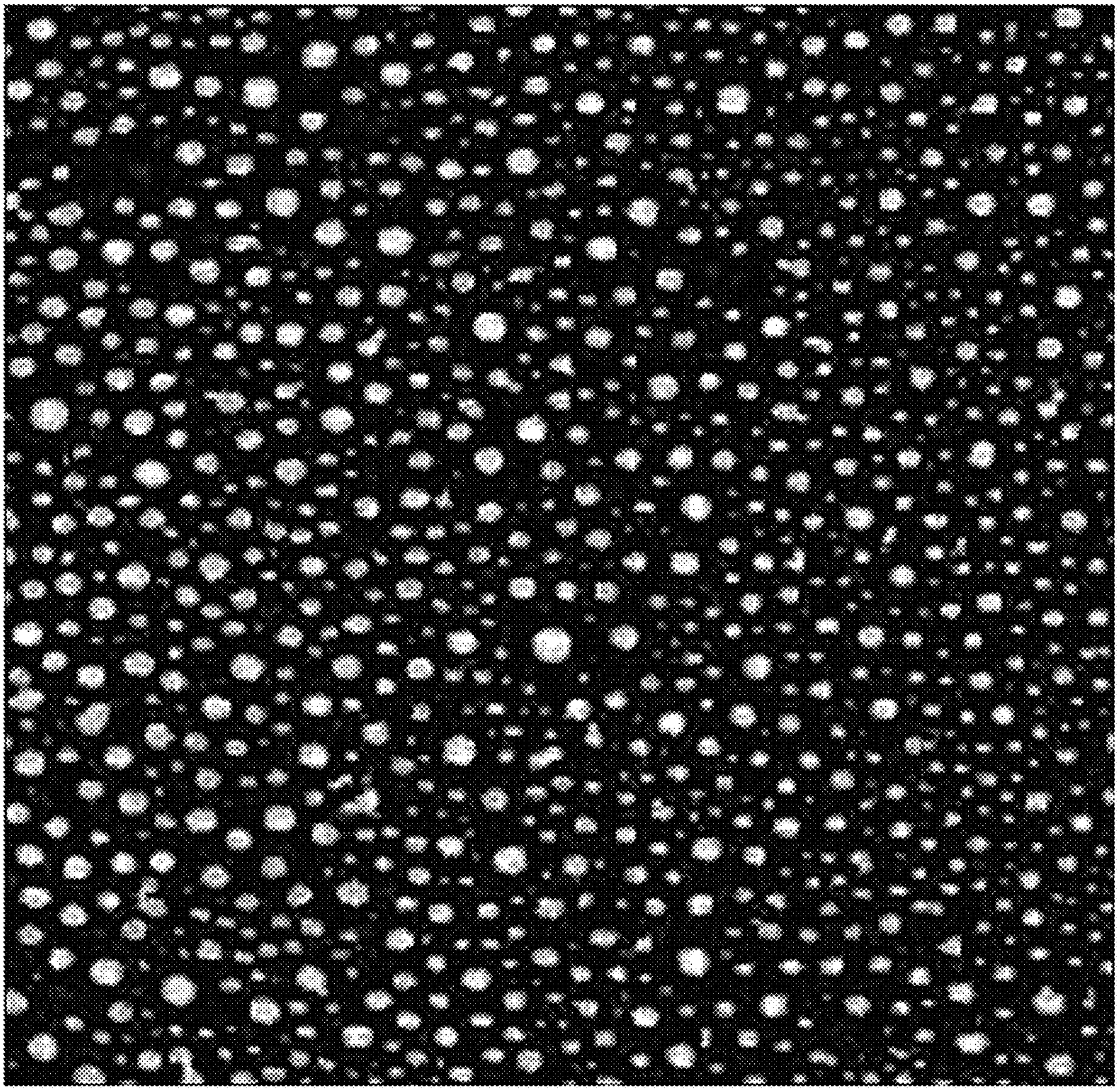
Figure 3D:
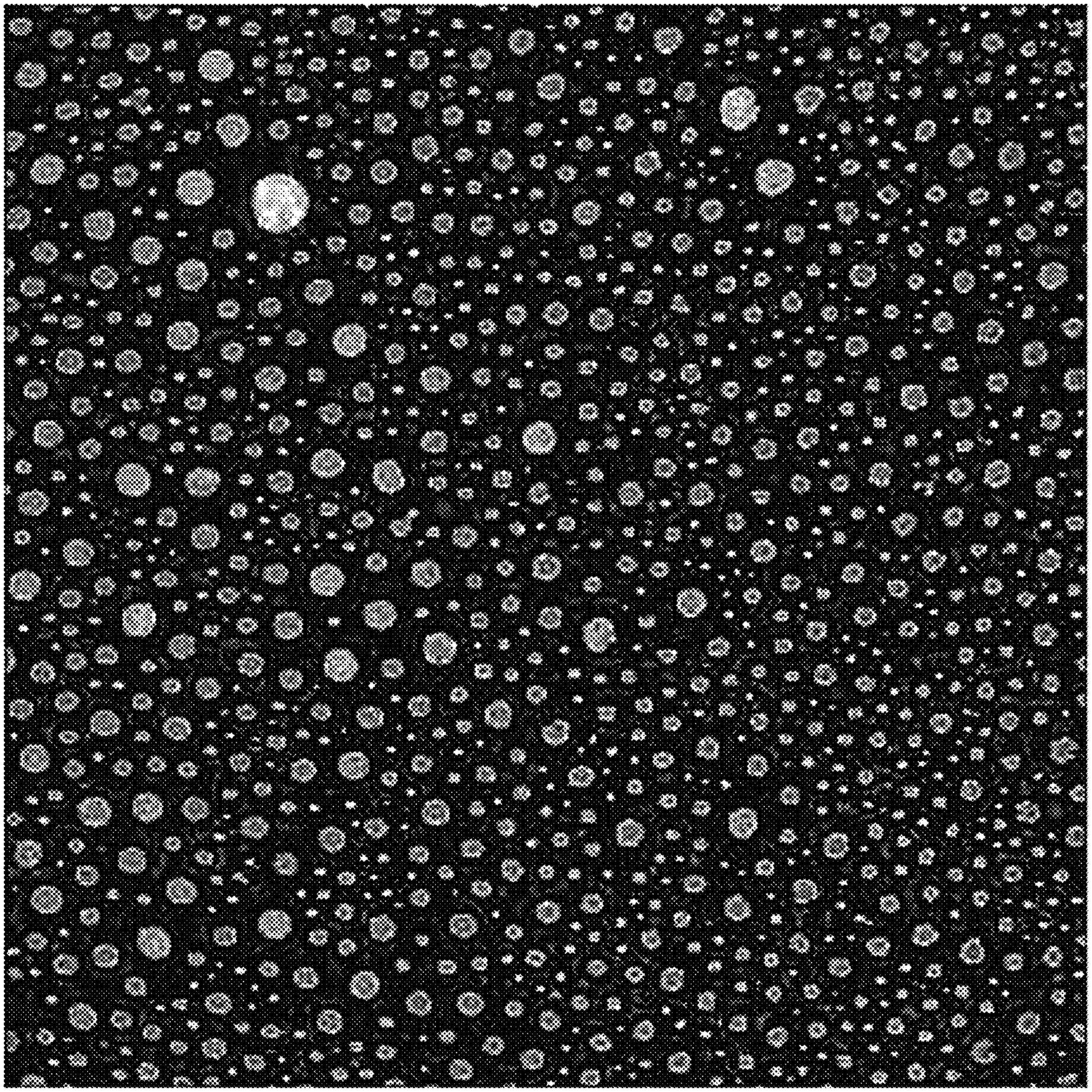
Figure 3E:
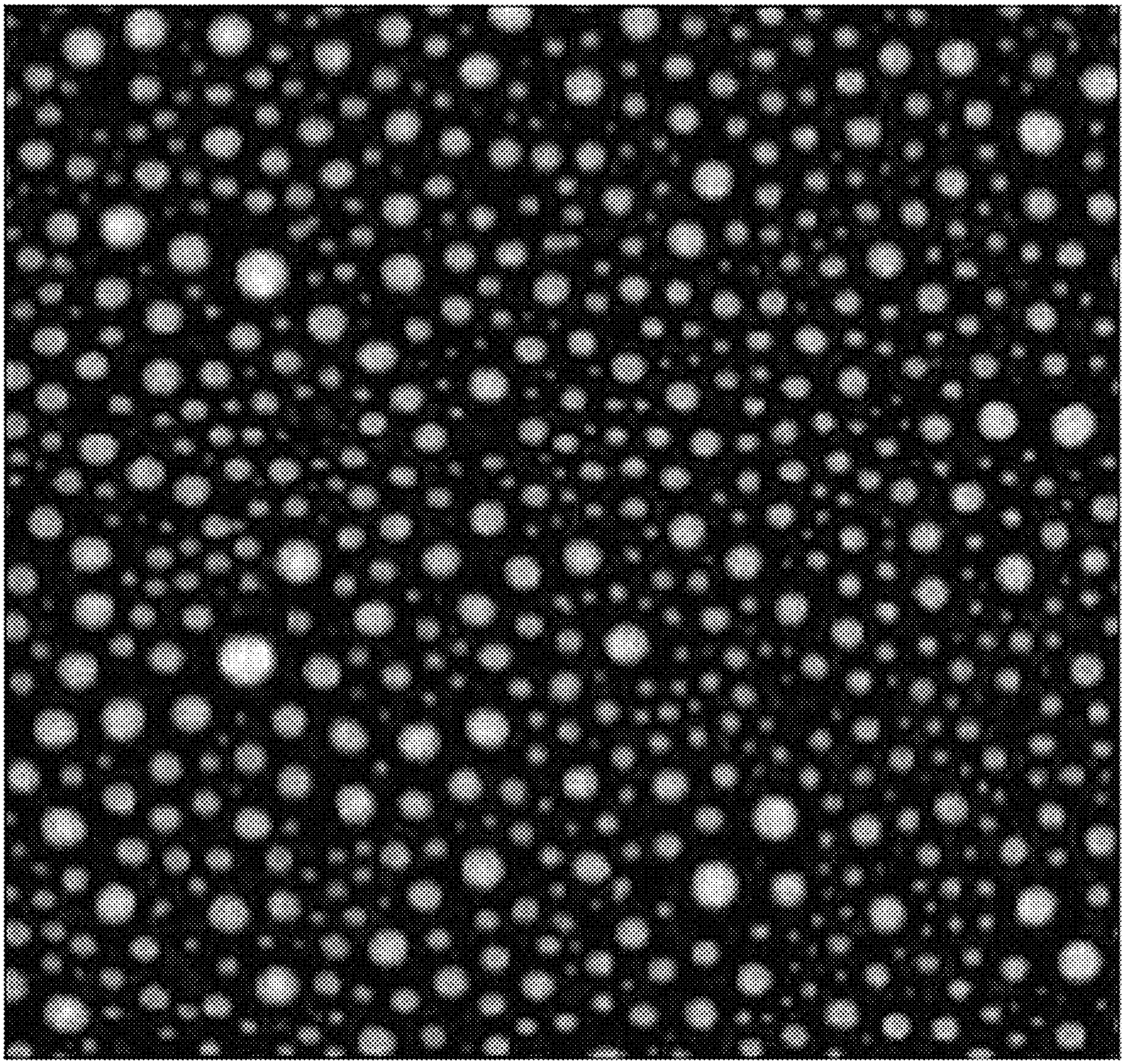
Figure 3F:
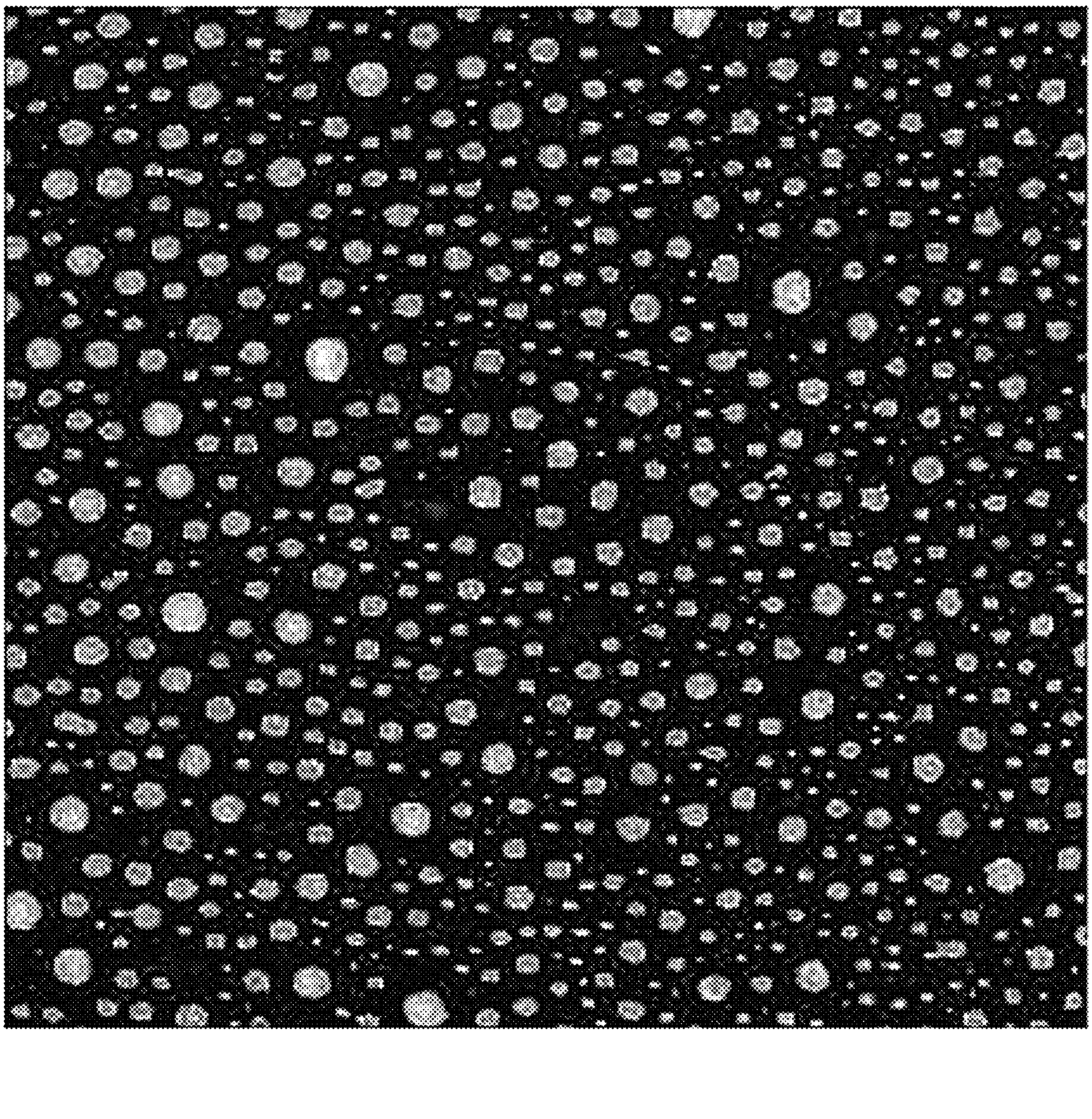

| | Diutan gum | Xanthan gum | Cellulose gum |
|---|---|---|---|
| Structure | FIG. 2A | FIG. 2B | FIG. 2C |
| Bubble density | 150 | 135 | 107 |
| | FIG. 2D | FIG. 2E | FIG. 2F |
| Bubble elasticity | 12000 | 10300 | 8300 |

3. Mixed Use of Guar Gum and Diutan Gum

Figure 4A:
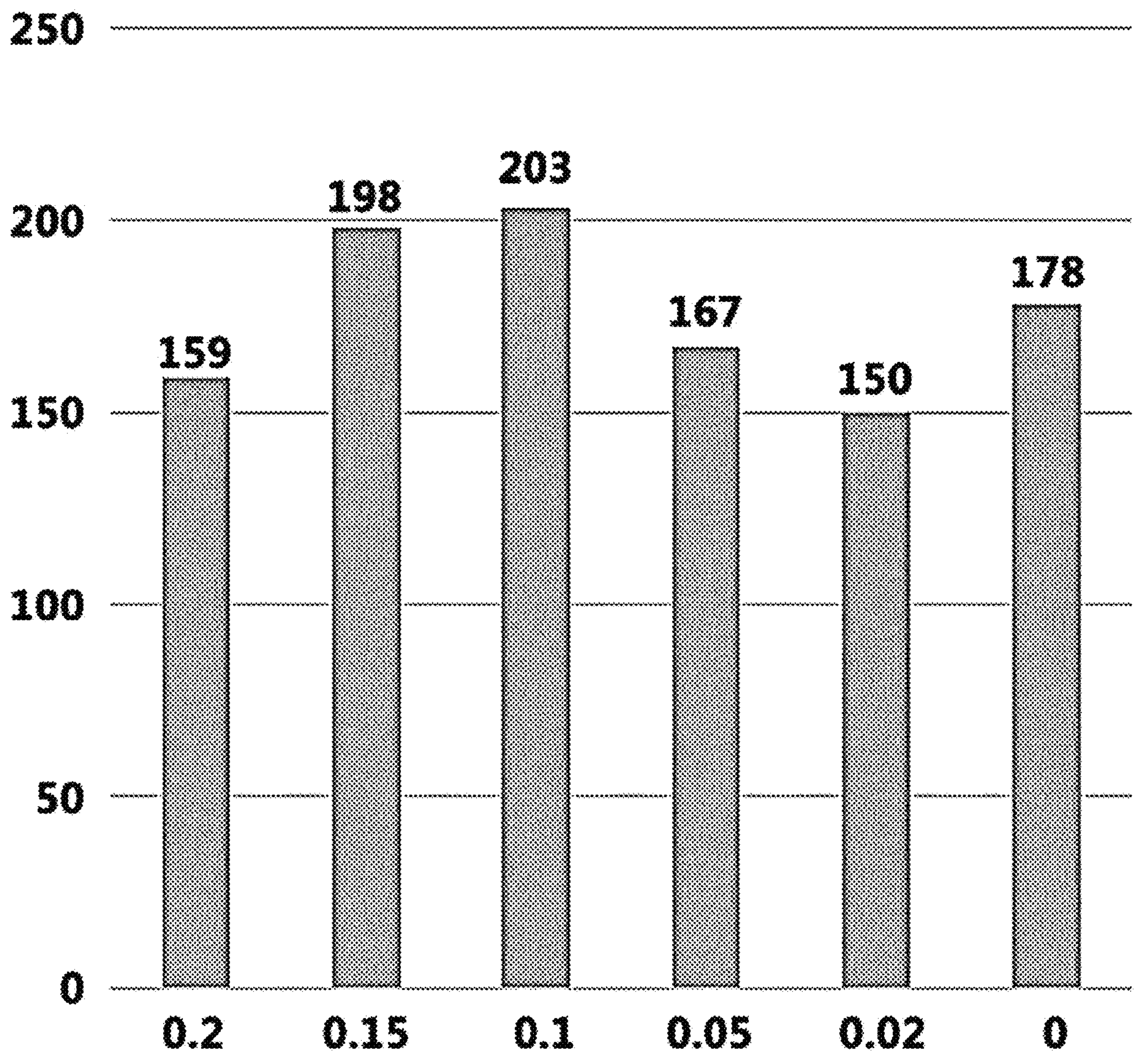
FIGS. 4A and 4B are graphs showing bubble density (4A) and bubble elasticity (4B) that vary depending on combination ratio of a composition according to an embodiment of the present disclosure.
Figure 4B:
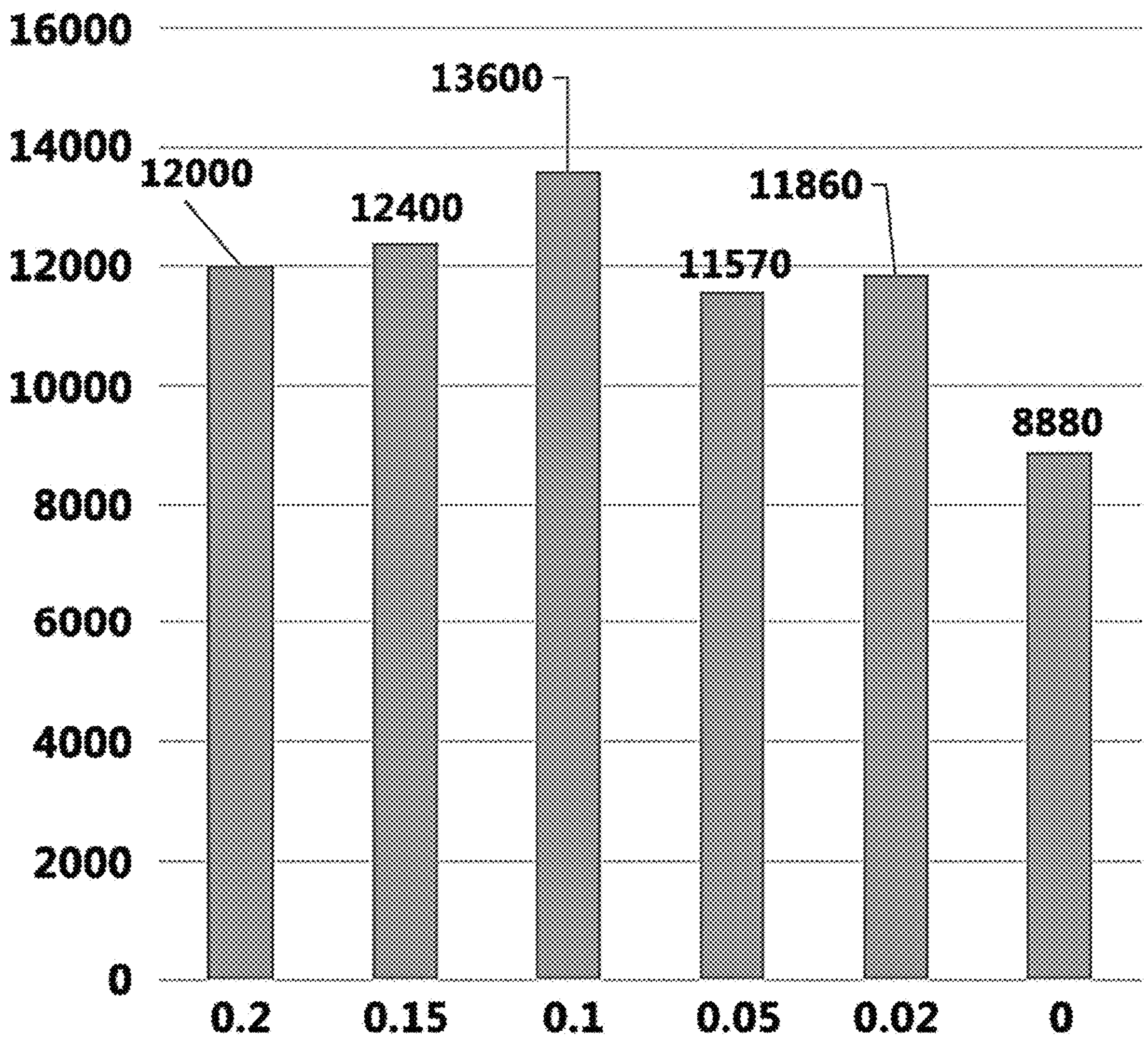

As shown in Table 4. Table 5, and FIGS. 4A and 4B below, a synergistic effect of improving the bubble power was confirmed by combining the guar gum, which increased the bubble density, with the diutan gum, which had the effective bubble elasticity. Various compositions were prepared by fixing a total content of the guar gum and the diutan gum to 0.2% by weight based on the total weight of the composition, and setting a content of the diutan gum to 0 to 0.2% by weight. Photographs observing the bubble density of each composition were shown in FIGS. 3A to 3F, respectively, and the results of the bubble density (4A) and the bubble elasticity (4B) were shown in the graphs.

TABLE 4

| | Component name | Mixing ratio of guar gum:diutan gum Example 2 | Example 3 | Example 4 | Example 5 |
|---|---|---|---|---|---|
| Prescription of weakly acidic amino acid-based cleanser base | Purified water (KP) | to 100 | to 100 | to 100 | to 100 |
| | Glycerin | 20.000 | 20.000 | 20.000 | 20.000 |
| | Potassium cocoylglycinate | 15.000 | 15.000 | 15.000 | 15.000 |
| | Purified water * Laurylhydroxysultaine | 1.000 | 1.000 | 1.000 | 1.000 |
| | Citric acid | 1.500 | 1.500 | 1.500 | 1.500 |
| Guar gum | Hydroxypropylguarhydroxypropyltrimonium chloride | 0.05 | 0.1 | 0.15 | 0.18 |
| Diutan gum | Diutan gum | 0.15 | 0.1 | 0.05 | 0.02 |
| Amount of bubbles | | Much | Much | Much | Much |
| Bubble density | | 198 | 203 | 167 | 150 |
| Bubble elasticity | | 12,400 | 13,600 | 11,570 | 11,860 |
| Slippery | | Good | Good | Good | Good |

TABLE 5

| Guar gum (unit: wt. %) | Diutan gum (unit: wt. %) | Bubble density | Bubble elasticity |
|---|---|---|---|
| 0 | 0.2 | 159 (FIG. 3A) | 12000 |
| 0.05 | 0.15 | 198 (FIG. 3B) | 12400 |
| 0.1 | 0.1 | 203 (FIG. 3C) | 13600 |
| 0.15 | 0.05 | 167 (FIG. 3D) | 11570 |
| 0.18 | 0.02 | 150 (FIG. 3E) | 11860 |
| 0.2 | 0 | 178 (FIG. 3F) | 8880 |

As a result of the observation, it could be confirmed that when the guar gum and the diutan gum were combined in a ratio of 1:1, the bubble density (FIG. 4A) and the bubble elasticity (FIG. 4B) were the best.

As a result, it could be confirmed that the natural gums alone did not have a significant effect on the bubble power, whereas when the cationic polymer was combined with the polysaccharide polymer that has a slippery feeling of use but can thicken the water phase, it was possible to increase both of the bubble density and the bubble elasticity while maintaining an amount of the bubbles.

4. Comparison with Commercial Product

Figure 5A:
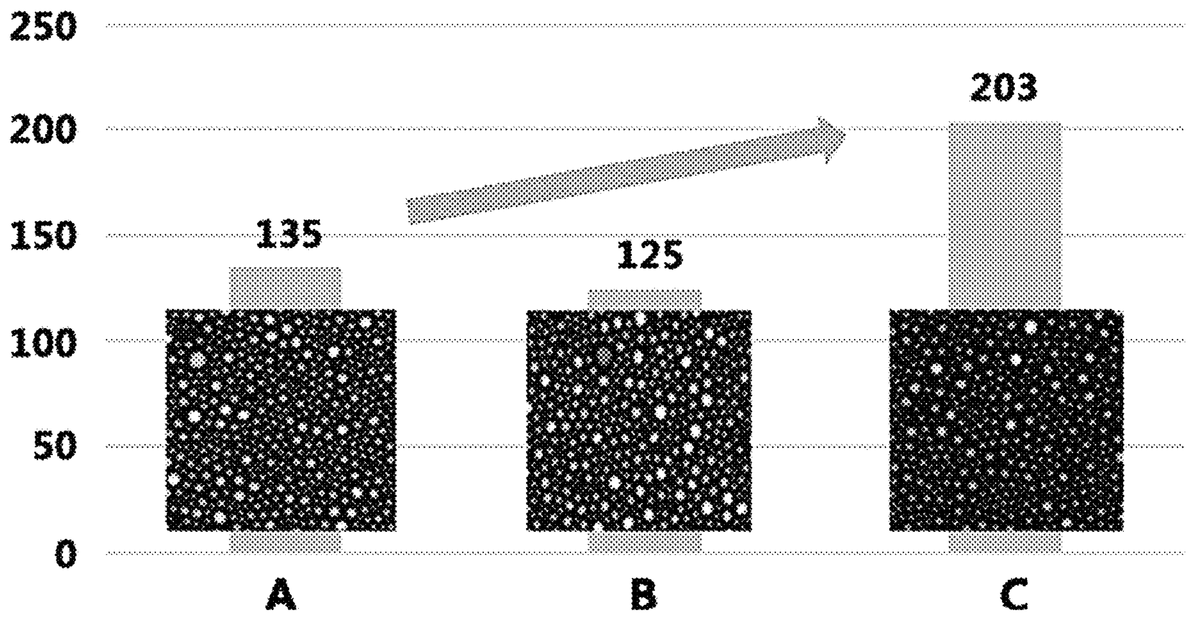
FIGS. 5A and 5B are graphs showing bubble density (5A) and bubble elasticity (5B) of a composition according to an embodiment of the present disclosure and a commercial product.
Figure 5B:
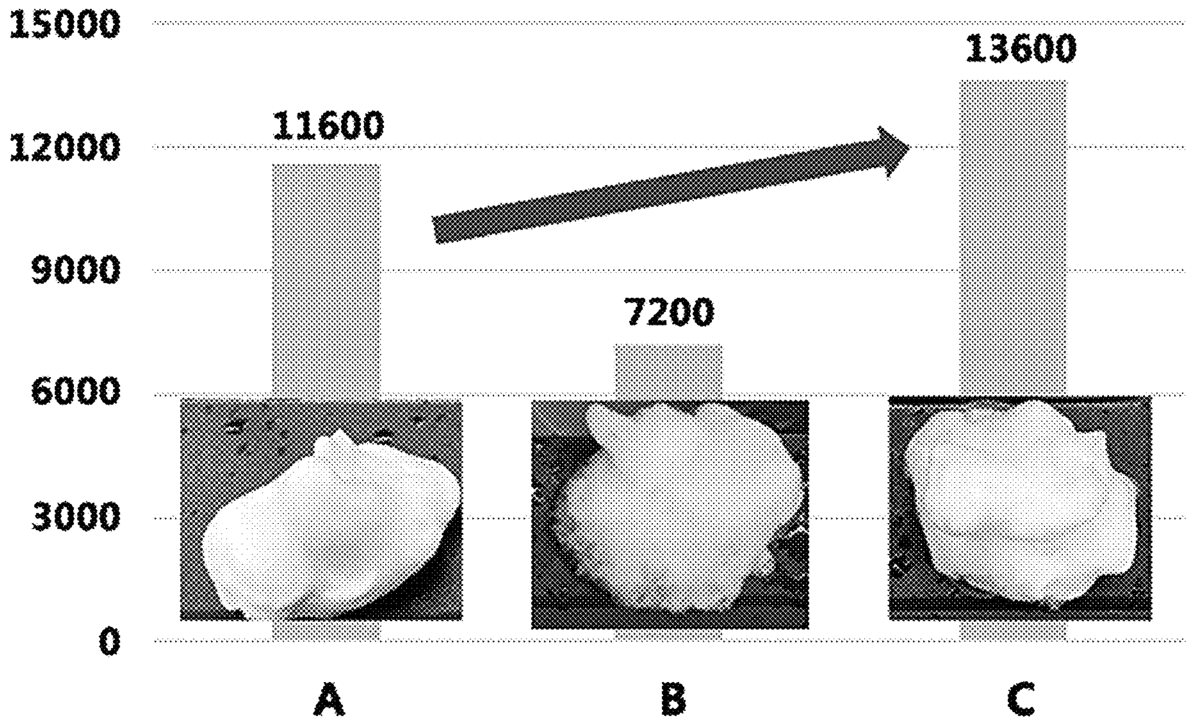

As shown in FIGS. 5A and 5B, HB Mommy Soap (Happy Bath Micro Micellar Deep Cleansing Foam) and HB Amino Acid (Happy Bath Micro Micellar Weakly Acidic Deep Cleansing Foam) as the conventional products, and the soap prepared by Example 3 and having a weight ratio of the guar gum: the diutan gum of 1:1 were compared in relation to their bubble density (FIG. 5A) and bubble elasticity (FIG. 5B). In FIGS. 5A and 5B. A shows the HB Mommy Soap, B shows the HB amino acid, and C shows Example 3. As a result of the comparison, it could be confirmed that through combination of two types of the natural gums with different ionic properties, the soap prepared by Example 3 showed an effect of increasing the bubble density and the bubble elasticity by 50% and 17% compared to the soap-type cleanser (HB Mommy Soap).

What is claimed is:

1. A method for improving bubble density and bubble elasticity of a weakly acidic skin cleanser, comprising:

a step of adding a diutan gum to the weakly acidic skin cleanser, wherein the weakly acidic skin cleanser further comprises an amino acid-based surfactant, and wherein a pH of the weakly acidic skin cleanser is 4 to 7.

2. The method according to claim 1, wherein the weakly acidic skin cleanser further comprises a cationic polymer.

3. The method according to claim 2, wherein the cationic polymer is a guar gum.

4. The method according to claim 1, wherein the weakly acidic skin cleanser further comprises a cationic polymer, and a weight ratio of the cationic polymer and the diutan gum is 1:0.5 to 2.

5. The method according to claim 1, wherein the weakly acidic skin cleanser further comprises a cationic polymer, and a total weight of the cationic polymer and the diutan gum is 0.05 to 1% by weight based on the total weight of the weakly acidic skin cleanser.

6. The method according to claim 1, wherein the bubble elasticity of the weakly acidic skin cleanser is 11,000 cps or more when measured by a BROOKFIELD LV viscometer.

7. The method according to claim 1, wherein the weakly acidic skin cleanser is a hair cleanser, a body cleanser, a hand cleanser, or a face cleanser.

8. A composition for skin cleansing, comprising a diutan gum and an amino acid-based surfactant, wherein a pH of the composition is 4 to 7.

9. The composition for skin cleansing according to claim 8, further comprising a cationic polymer.

10. The composition for skin cleansing according to claim 9, wherein the cationic polymer is a guar gum.

11. The composition for skin cleansing according to claim 8, wherein the composition further comprises a cationic polymer, and a weight ratio of the cationic polymer and the diutan gum is 1:0.5 to 2.

12. The composition for skin cleansing according to claim 8, wherein the composition further comprises a cationic polymer, and a total weight of the cationic polymer and the diutan gum is 0.05 to 0.5% by weight based on the total weight of the composition.

13. The composition for skin cleansing according to claim 8, wherein a bubble elasticity of the composition is 11,000 cps or more when measured by a BROOKFIELD LV viscometer.

14. The composition for skin cleansing according to claim 8, wherein the composition is a hair cleanser, a body cleanser, a hand cleanser, or a face cleanser.

* * * * *